United States Patent
Amthor

(10) Patent No.: US 12,061,705 B2
(45) Date of Patent: Aug. 13, 2024

(54) SECURE REMOTE IMAGE ANALYSIS BASED ON RANDOMIZED DATA TRANSFORMATION

(71) Applicant: KONINKLIJKE PHILIPS N.V., Eindhoven (NL)

(72) Inventor: Thomas Erik Amthor, Hamburg (DE)

(73) Assignee: Koninklijke Philips N.V., Eindhoven (NL)

( * ) Notice: Subject to any disclaimer, the term of this patent is extended or adjusted under 35 U.S.C. 154(b) by 778 days.

(21) Appl. No.: 15/734,282

(22) PCT Filed: Jun. 11, 2019

(86) PCT No.: PCT/EP2019/065148
§ 371 (c)(1),
(2) Date: Dec. 2, 2020

(87) PCT Pub. No.: WO2019/243110
PCT Pub. Date: Dec. 26, 2019

(65) Prior Publication Data
US 2021/0224403 A1    Jul. 22, 2021

Related U.S. Application Data

(60) Provisional application No. 62/686,185, filed on Jun. 18, 2018.

(51) Int. Cl.
*G06F 21/60* (2013.01)
*G06T 7/00* (2017.01)
(Continued)

(52) U.S. Cl.
CPC .......... *G06F 21/602* (2013.01); *G06T 7/0012* (2013.01); *G16H 30/40* (2018.01);
(Continued)

(58) Field of Classification Search
CPC ............ H04L 63/0428; H04L 2209/60; G06T 2207/20021; G06T 7/0012;
(Continued)

(56) References Cited

U.S. PATENT DOCUMENTS 8,321,690 B2 * 11/2012 Oliveira ............. H04N 21/8355
380/37
9,270,947 B2 * 2/2016 Tanaka ................ H04N 21/4405
(Continued)

FOREIGN PATENT DOCUMENTS

KR         101751971      6/2017

OTHER PUBLICATIONS

Azoug et al., "Double image encryption based on the reciprocal-orthogonal parametric transform and chaotic maps," 2013 8th International Workshop on Systems, Signal Processing and their Applications (WoSSPA) Year: 2013 | Conference Paper | Publisher: IEEE.*

(Continued)

*Primary Examiner* — Roderick Tolentino

(57) ABSTRACT

A non-transitory storage medium stores instructions readable and executable by a first computer (14) to perform an image processing method (100, 200, 400). The method includes: encrypting image data portions to generate encrypted image data portions; transmitting the encrypted image data portions from the first computer to a second server (16) different from the first computer; decrypting encrypted processed image data portions received at the first computer from the second server to produce processed image data portions and generating a processed image from the processed image data portions; and controlling a display device (24) to display the processed image or storing the processed image in a database (30).

14 Claims, 4 Drawing Sheets

(51) Int. Cl.
*G16H 30/40* (2018.01)
*H04L 9/40* (2022.01)
*G06F 21/10* (2013.01)

(52) U.S. Cl.
CPC ...... *H04L 63/0428* (2013.01); *G06F 21/1083* (2023.08); *G06F 2221/2123* (2013.01); *G06F 2221/2125* (2013.01); *G06T 2207/10088* (2013.01); *G06T 2207/30004* (2013.01)

(58) Field of Classification Search
CPC . G06T 2207/10088; G06T 2207/30004; G06F 21/6245; G06F 2221/2107; G06F 21/602; G06F 2221/0784; G16H 30/40
See application file for complete search history.

(56) References Cited

U.S. PATENT DOCUMENTS

| | | | | |
|---|---|---|---|---|
| 11,057,214 | B2* | 7/2021 | Kim | G06F 21/35 |
| 2001/0037464 | A1* | 11/2001 | Persels | H04L 69/08 |
| | | | | 726/5 |
| 2004/0190795 | A1* | 9/2004 | Funahashi | H04L 63/18 |
| | | | | 358/1.15 |
| 2011/0135089 | A1* | 6/2011 | Bae | H04N 21/2347 |
| | | | | 380/200 |
| 2013/0208966 | A1 | 8/2013 | Zhao | |
| 2013/0246803 | A1* | 9/2013 | Vale | H04L 65/612 |
| | | | | 711/E12.001 |
| 2015/0347682 | A1 | 12/2015 | Chen | |
| 2016/0110564 | A1 | 4/2016 | Tsang | |
| 2016/0110632 | A1 | 4/2016 | Kiraly | |
| 2016/0219024 | A1 | 7/2016 | Verzun | |
| 2017/0126672 | A1* | 5/2017 | Jang | H04L 63/0492 |
| 2017/0200256 | A1 | 7/2017 | Wiemker | |
| 2017/0206523 | A1* | 7/2017 | Goeringer | G06Q 20/3827 |
| 2017/0371601 | A1* | 12/2017 | Kaneko | G06F 3/1222 |
| 2018/0338740 | A1* | 11/2018 | Behrooz | G06T 7/187 |

OTHER PUBLICATIONS

Maan et al., "Image encryption based on Walsh Hadamard and fractional fourier transform using Radial Hilbert Mask," 2017 International Conference on Computing and Communication Technologies for Smart Nation (IC3TSN) Year: 2017 | Conference Paper | Publisher: IEEE.*

International Search Report and Written Opinion Dated Aug. 14, 2019 for International Application No. PCT/EP2019/065148 Filed Jun. 11, 2019.

Gomathisankaran, et al: "Ensure privacy and security in the process of medical image analysis", 2013 IEEE International Conference on Granular Computing (GRC), IEEE, Dec. 13, 2013.

Sathishkumar, et al: "Image Encryption Using Random Pixel Permutation by Chaotic Mapping", 2012 IEEE Symposium on Computers & Informatics.

Usman, et al: "Medical Image Encryption Based on Pixel Arrangement and Random Permutation for Transmission Security", 2007 IEEE.

* cited by examiner

SECURE REMOTE IMAGE ANALYSIS BASED ON RANDOMIZED DATA TRANSFORMATION

CROSS REFERENCE TO RELATED APPLICATIONS

This application is the U.S. National Phase application under 35 U.S.C. § 371 of International Application No. PCT/EP2019/065148 filed Jun. 11, 2019, which claims the benefit of U.S. Provisional Patent Application No. 62/686,185 filed Jun. 18, 2018. These applications are hereby incorporated by reference herein.

FIELD

The following relates generally to the image processing arts, image analysis arts, image encryption and decryption arts, and related arts.

BACKGROUND

Remote image processing can provide a range of possible benefits. By performing some or all image processing at a cloud-based resource, greater computing power can be brought to bear on the image processing task. Remote image processing can also be implemented in a fee-for-service model, thereby making advanced processing techniques developed by a service provider available to a wide range of clinical customers. For example, such a fee-for-service model would enable a service provider to market proprietary image processing techniques to customers without the risk of reverse engineering which is present when the actual processing code is supplied to the customer. Cloud-based remote image processing also facilitates efficient updating of image processing algorithms, with such updates immediately propagated to customers.

However, transfer and remote analysis of medical images raises concerns about privacy and data security. Remote image processing, e.g. through cloud computing, require image data to be sent to the remote server. In one possible approach, the image data are encrypted at the client-side and transmitted in encrypted form to the server, where the image data are decrypted, processed, and the processed image data re-encrypted and transmitted back to the client side for final decryption and clinical use. In this approach the unencrypted image is present at the server, and this may cause privacy issues, since the image could potentially be stored outside the secure hospital network. Moreover, the approach requires use of an encryption architecture that allows for remote decryption at the server, and the shared crypto-key or other mechanism employed for this may be a further source of vulnerability.

The following discloses new and improved systems and methods to overcome these problems.

SUMMARY

In one disclosed aspect, a non-transitory storage medium stores instructions readable and executable by a first computer to perform an image processing method. The method includes: encrypting image data portions to generate encrypted image data portions; transmitting the encrypted image data portions from the first computer to a second server different from the first computer; decrypting encrypted processed image data portions received at the first computer from the second server to produce processed image data portions and generating a processed image from the processed image data portions; and controlling a display device to display the processed image or storing the processed image in a database.

In another disclosed aspect, an image processing assistance device includes a server; and a non-transitory storage medium storing instructions readable and executable by the server to perform an image processing assistance method including: receiving encrypted image data portions from a client computer via an electronic data network; processing the encrypted image data portions to produce processed encrypted image data portions wherein the processing does not include decrypting the encrypted image data portions; and transmitting the processed encrypted image data portions to the client server via the electronic data network.

In another disclosed aspect, an image processing method includes: at a first computer, encrypting image data portions to generate encrypted image data portions; at a second server, processing the encrypted image data portions to produce processed encrypted image data portions; at the first computer, decrypting the encrypted processed image data portions to produce processed image data portions and generating a processed image from the processed image data portions; and controlling a display device to display the processed image or storing the processed image in a database.

In another disclosed aspect, an image processing method includes: at a first computer, generating a data stream comprising the image data portions including mixing an ordering of the image data portions in the data stream; transmitting the data stream from the first computer to a second server; at the second server, processing the image data portions to produce processed image data portions and transmitting the processed image data portions from the second server to the first computer; at the first computer, generating a processed image from the processed image data portions; and controlling a display device to display the processed image or storing the processed image in a database.

One advantage resides in providing remote image processing with strictly client-side encryption ensuring patient privacy.

Another advantage resides in providing remote image processing without the need to share a crypto-key or other decryption tool with the remote server performing the remote image processing.

Another advantage resides in ensuring data security of transmitted images.

Another advantage resides in providing remote image processing in which the medical images are transmitted with randomization factors.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The disclosure may take form in various components and arrangements of components, and in various steps and arrangements of steps. The drawings are only for purposes of illustrating the preferred embodiments and are not to be construed as limiting the disclosure.

DETAILED DESCRIPTION

Some current image analysis techniques rely on multi-dimensional measurements per voxel/pixel and require complex algorithms, such as finding constituents in high-dimensional spatially resolved spectroscopic measurements (e.g., optical spectroscopy or MR spectroscopy), or tissue characterization using MR Fingerprinting, or artificial intelligence to provide assistance in diagnosis. Other image analysis techniques may need to consider spatial correlations, such as the determination of tissue conductivity from MR phase maps. In this case, the multi-dimensional data set would consist of a small patch containing several voxels.

The disclosed approaches are applicable to situations in which the image processing provided by the cloud server is spatially localized, e.g. processing of multidimensional voxel data (spectral, MR fingerprinting data) on a per-voxel basis, or processing of small voxel patches (e.g. for conductivity analysis, applying a small-area kernel filter), or otherwise-defined image data portions which are processed independently of one another. The approach employs client-side encryption of the multidimensional data of each image data portion, e.g. each voxel or voxel patch, and optionally further employs randomization (i.e. mixing) of the encrypted voxels or voxel patches.

The client-side encryption of individual voxels, voxel patches, or other image data portions should be designed to ensure that the cloud server can still perform the intended processing on the encrypted voxel or voxel patch, followed by client-side decryption of the processed encrypted voxel or voxel patch. As examples, in many spectral analyses the data may be scaled by a random scaling factor (which may be different for each voxel) without impacting the spectral analysis; while, for tissue conductivity analysis of a voxel patch the data may be encrypted by mirroring or rotation in space, again optionally employing a different spatial transform for each voxel patch.

In some variant embodiments, the randomization of the voxels or voxel patches can include mixing voxels or voxel patches of different images, adding "dummy" voxels or voxel patches, and/or employing an intervening proxy or relay server to prevent grouping of voxels or voxel patches corresponding to an image.

Embodiments disclosed herein employ both voxel or patch encryption and randomization (i.e. mixing) of the voxels or patches, but it is contemplated to omit one of these. In particular, omitting the encryption of voxels or patches may be useful or even necessary if a suitable transform cannot be identified that still permits the intended cloud-based per-voxel or per-patch processing. Preferably, when encryption is employed, the parameters of the transform used to encrypt each voxel or patch should be randomized.

Figure 1:
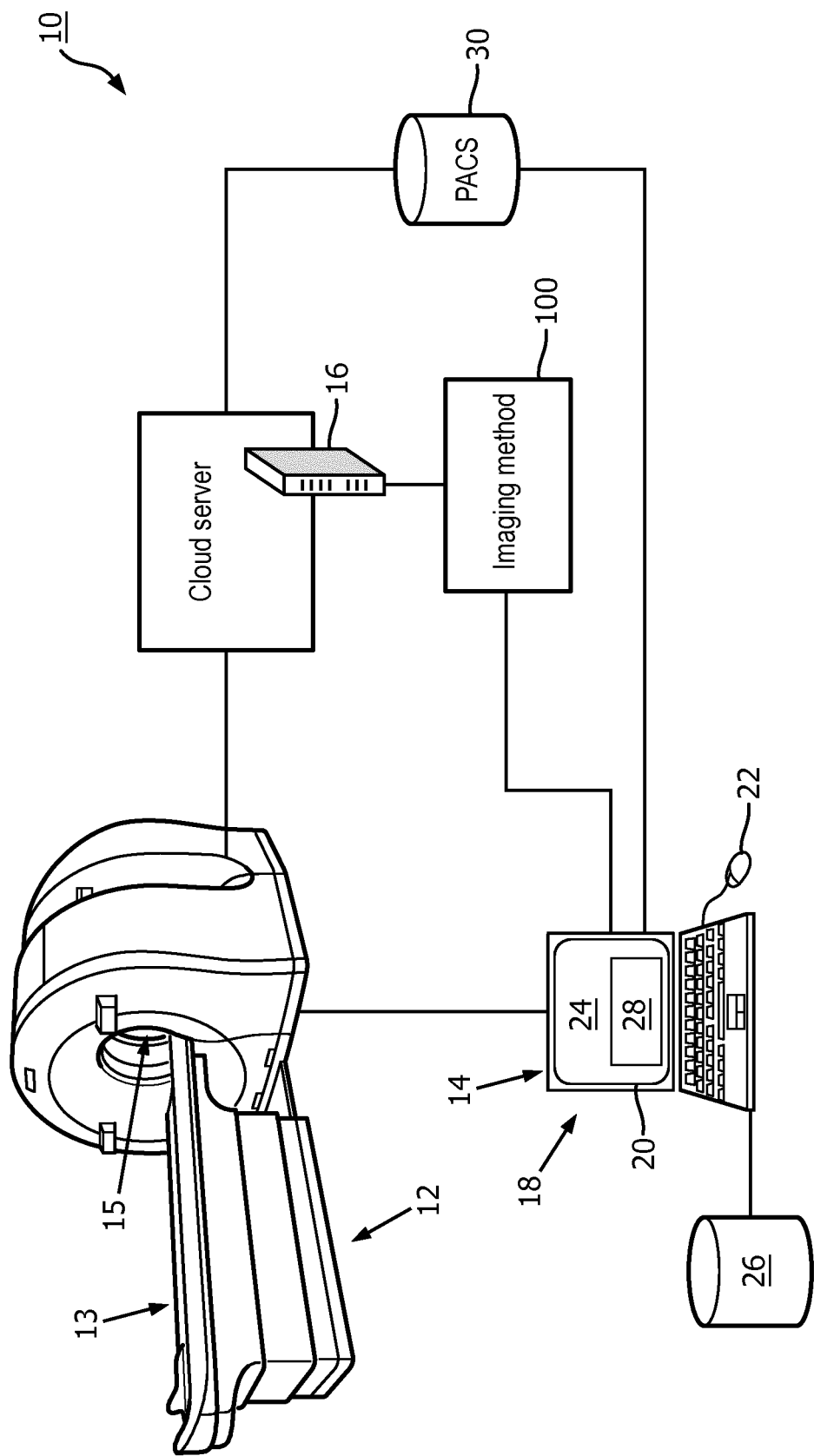
FIG. 1 diagrammatically shows an image processing assistance system according to one aspect.

With reference to FIG. 1, an illustrative image acquisition and processing device or system 10 is shown. As shown in FIG. 1, the system 10 includes an imaging or image acquisition device 12; a first or client computer 14, and a second or cloud-based server computer 16. In one example, the image acquisition device 12 can comprise a PET imaging device including a PET gantry and an array of radiation detectors (not shown); typically, the radiation detectors of the PET gantry are arranged as a series of PET detector rings arranged to span an axial FOV). In another example, imaging device 12 can comprise a gamma camera of a SPECT imaging device, e.g. including one, two, three, or more radiation detector heads each arranged on a robotic gantry to move around the patient to provide tomographic data, and each radiation detector head of the gamma camera typically having a honeycomb collimator or other type of collimator to limit the vantage of the radiation detectors to lines or narrow-angle conical fields of view. In another example, the imaging device 12 can comprise a CT gantry and array of radiation detectors (not shown). In another example, the imaging device 12 can comprise a MR imaging device. The illustrative imaging device 12 is a multimodality PET/CT imaging device with PET and CT gantries. A patient table (or bed) 13 is arranged to load a patient into an examination region 15 of the imaging device 12.

The first computer 14 is operable by a medical professional (e.g., a doctor, a nurse, a radiology technician, and so forth). The first computer 14 can comprise a desktop computer, server computer, combination thereof, or other electronic data processing device 18 with typical components, such as at least one electronic processor 20, at least one user input device (e.g., a mouse, a keyboard, a trackball, and/or the like) 22, and a display device 24. It should be noted that these components can be variously distributed. For example, the electronic processor 20 may include a local processor of a workstation terminal and the processor of a hospital server computer that is accessed by the workstation terminal over a secure hospital network (individual components not shown in FIG. 1). In some embodiments, the display device 24 can be a separate component from the computer 18. The first computer 14 can also include or have secure access to one or more databases or non-transitory storage media 26 (such as a magnetic disk, RAID, or other magnetic storage medium; a solid state drive, flash drive, electronically erasable read-only memory (EEROM) or other electronic memory; an optical disk or other optical storage; various combinations thereof; or so forth). The display device 24 is configured to display a graphical user interface (GUI) 28 including one or more fields to receive a user input from the user input device 22.

The system 10 also includes the second server 16 which is typically a cloud-based server. The overall system of FIG. 1 represents a remote image processing setup in which an image acquired and/or under control of a hospital or other medical institution that controls the first computer 14 is to send image data for processing to the second server 16 which is outside of the secure data system under control of the hospital or other medical institution. The first computer 14 is part of a secure data network, e.g. is operatively connected in a Picture Archiving and Communication System (PACS) database 30 via a secure hospital data network for storing images therein. On the other hand, the second server 16 is a remote server in the sense that it is not part of the secure hospital network or is otherwise situated such that the hospital or other medical institution that controls the first computer 14 does not have control over the second server 16. As such, the hospital or other medical institution does not have direct assurance that the second server 16 is secure from data theft or other cyber security breaches. This lack of direct control over the remote server 16 can have significant consequences. For example, hospital data security rules and/or governing jurisdictional statutes or laws pertaining to cybersecurity of medical data may prohibit transfer of medical data (including medical image data) to the remote second server 16 without suitable assurance that the medical data will remain secure and that patient privacy is not compromised.

Conventionally, this can be a problem in a remote image processing architecture because, while the image may be encrypted when sent to the remote server, it is then decrypted at the remote server in order to perform the image processing, and then the processed image is re-encrypted for transmission back to the first (e.g. client) system. This presents at least two opportunities for breach of data security. First, the data is not encrypted at the remote server, and that remote server is not under control of the hospital or other medical institution. Second, to perform the image decryption and processed image encryption operations at the remote server, there must be some shared crypto-key or the like that is shared between the hospital and the remote server. While use of techniques such as public key or asymmetrical cryptography can at least partially address the latter concern about the shared crypto-key, such nonetheless presents a potential security weakness.

In embodiments disclosed herein, a more secure remote image processing setup is provided in which no crypto-key is shared with the remote server, and the remote server never has access to the unencrypted image. Thus, even if the remote server 16 were to experience a security breach, this breach of the remote server 16 would not present a possibility of compromise the image data that is supplied to the remote server 16.

The second server 16 is operatively connected with a non-transitory storage medium (not shown) that stores instructions which are readable and executable by the second server to perform disclosed operations including performing an image processing method or process 100. The non-transitory storage medium may, for example, comprise a hard disk drive, RAID, or other magnetic storage medium; a solid state drive, flash drive, electronically erasable read-only memory (EEROM) or other electronic memory; an optical disk or other optical storage; various combinations thereof; or so forth. In some examples, the image processing method or process 100 may be performed by cloud processing.

While an illustrative image acquisition device 12 is described, it should be noted that in some embodiments a cloud-based image processing system or device may be provided which is a standalone system with no associated image acquisition device. For example, embodiments of the disclosed image processing device or system may be provided as a component of a radiology reading workstation, or as a component of a physician's computer, or so forth. In these cases, the image that is to undergo processing is suitably retrieved from the PACS or other database 30 which stores medical images.

Figure 2:
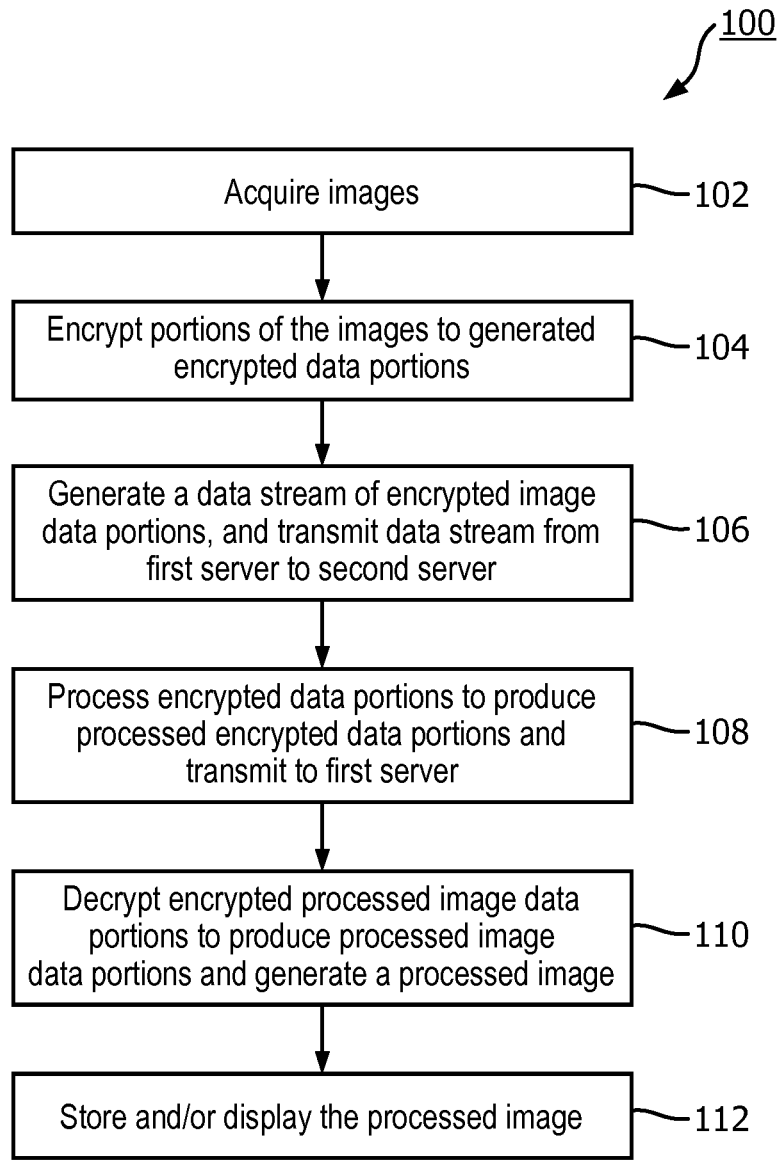
FIGS. 2-5 show exemplary flow chart operations of the system of FIG. 1.

With reference to FIG. 2, an illustrative embodiment of the imaging method 100 is diagrammatically shown as a flowchart. At 102, the image acquisition device 12 is operated to obtain one or more images of a patient. The image acquisition device 12 is controlled by the at least one electronic processor 20 of the first computer 14 to obtain the images.

At 104, the first computer 14 is programmed to encrypt image data portions of the acquired images to generate encrypted image data portions. In one example, the image data portions each comprise a magnetic resonance (MR) spectrum for a single voxel of an MR image. In another example, each image data portion comprises a patch of voxels, e.g. gray scale intensity values for each voxel of a 3×3 array of voxels of the image.

In some embodiments, the encrypting employs different encryption algorithms, or the same encryption algorithm with different encryption algorithm parameters, for encrypting different image data portions. The encrypting of each image data portion indexed by i can be expressed as the transform:

$$\tilde{S}_i = T(S_i, P_i) \quad \text{Equation (1)}$$

where $S_i$ represents multi-dimensional data of the image data portion indexed by i, T represents the transform, $P_i$ represents parameters of the transform T for the image data portion indexed by i, and $\tilde{S}$ represents the encrypted image data portion.

At 106, the first computer 14 is programmed to generate a data stream comprising the encrypted image data portions, which is then transmitted from the first computer 14 to the second server 16. In one example, the generating of the data stream comprises mixing an ordering of the encrypted image data portions in the data stream. In another example, the generating of the data stream comprises adding extra encrypted image data portions to the data stream wherein the resulting processed image data portions (to be described) corresponding to the extra encrypted image data portions are not used in generating the processed image. In a further example, the image data portions are extracted from two or more images, and the generating of the data stream comprises mixing the image data portions of the two or more images in the data stream.

At 108, the second server 16 is programmed to process the encrypted image data portions to produce processed encrypted image data portions. This is done without decrypting the encrypted image data portions. That is, the image processing is performed directly on the encrypted image data portions (as opposed to first decrypting the encrypted image data portions and then performing the processing on the decrypted image data portions). In one example, when each image data portion comprises an individual voxel MR spectrum, the processing of the encrypted image data portions includes applying a spectral imaging analysis or a magnetic resonance fingerprint analysis on a per-voxel basis to each individual voxel MR spectrum. In this example, the encrypting (at 104) comprises scaling each individual voxel MR spectrum by a voxel-specific scaling factor. This may be a different scaling factor for each voxel. This can be done since a decryption operation (described below) is done at first computer 14, which knows precisely which scaling factor it used for each voxel.

In another example, in which each image data portion comprises a patch of voxels, the processing of the encrypted image data portion includes applying a conductivity analysis or kernel filter analysis to each encrypted patch of voxels. In this example, the encrypting (at 104) comprises applying at least one of a spatial mirroring operation and a spatial rotation operation to the patch of voxels.

Again, the processing of the encrypted image data portions at the second server 16 to produce the processed encrypted image data portions does not include decrypting the encrypted image data portions at the second server 16. The image processing applied to the encrypted image data portions generated encrypted processed image data portions, and the second server 16 transmits the encrypted processed image data portions to the first computer 14.

At 110, the first computer 14 is programmed to decrypt the encrypted processed image data portions received from the second server 16 to produce processed image data portions, and to generate a processed image from the processed image data portions. In some embodiments, in which the data stream (generated at 106) comprises mixing the image data portions of the two or more images in the data stream, the generating of the processed image at 106 comprises generating a processed image corresponding to each image of the two or more images from the processed image data portions of that image. In some embodiments, in which the data stream (generated at 106) included "dummy" image data portions that are not actually part of the image, the corresponding "dummy" encrypted processed image data portions are discarded. Since the first computer 14 inserted these dummy image data portions, it has the requisite information to recognize the corresponding "dummy" encrypted processed image data portions. (By contrast, the second server 16, or a malicious entity that has breached security of the second server, has no way to know which received encrypted image data portions are dummy data).

At 112, the at least one electronic processor 20 of the first computer 14 is configured to control the display device 24 to display the processed image, or store the processed image in the PACS database 30.

In performing the decryption operation 110, the first computer 14 suitably leverages knowledge possessed at the first computer 14 as to the particular encryption algorithm and encryption algorithm parameters used to perform the encryption for each image data portion. Thus, for example, if the image data portions are MR spectra of individual voxels and a different (random or pseudorandom) scaling factor is used as the transform for encrypting each voxel, then the first computer 14 possesses the knowledge of which scaling factor was used to encrypt each voxel. By contrast, the second server 16, or a malicious entity that has breached security of the second server, has no way to know which scaling factor was used to encrypt each voxel, and hence has no way to decrypt the encrypted voxels. Hence, even if the second server 16 is breached by a malicious entity, that entity does not gain access to the underlying medical image—rather, the entity only gains access to the encrypted voxels with insufficient information in order to convert the encrypted voxels back to a medical image.

Figure 3:
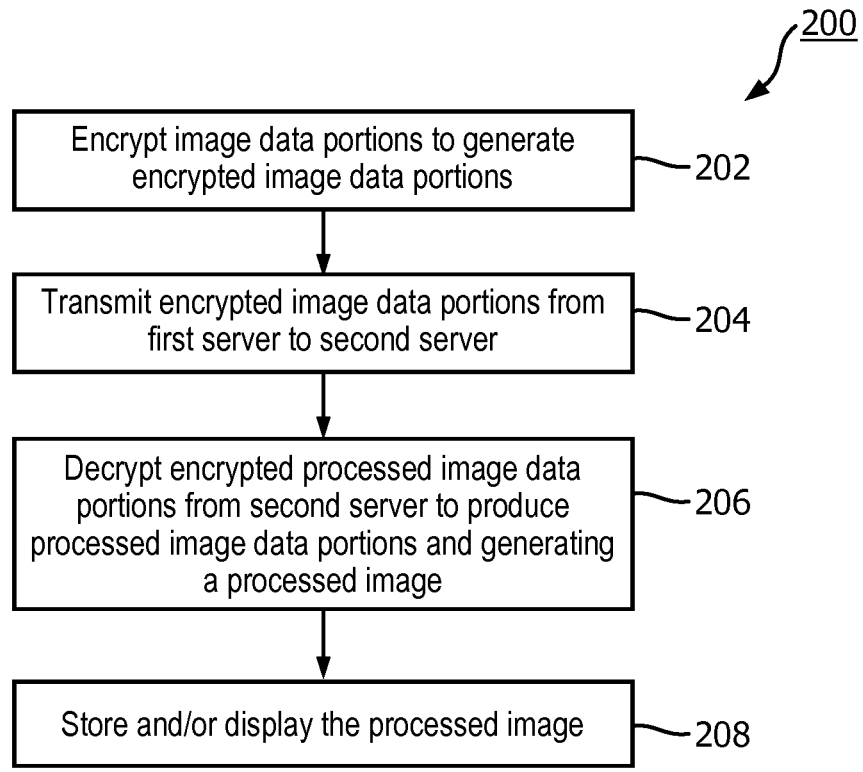
Figure 4:
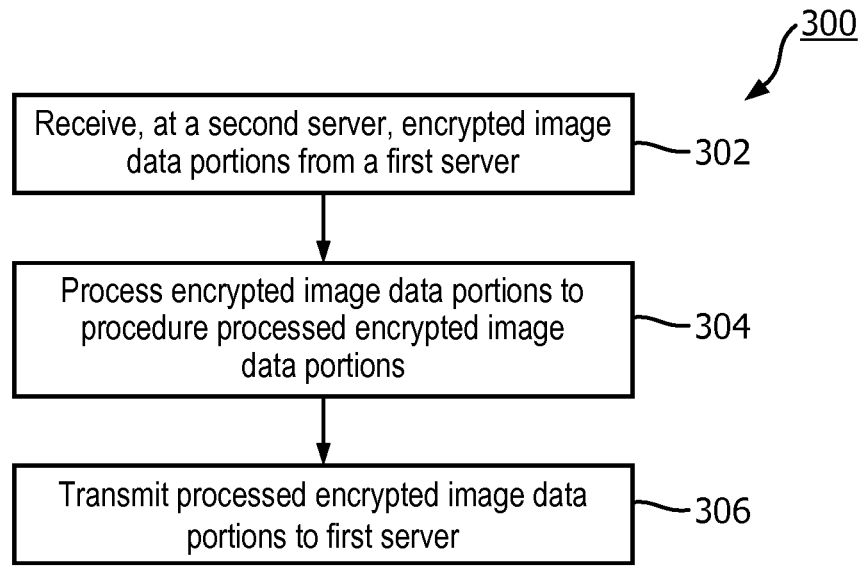

The imaging method 100 is described above in conjunction with both the first computer 14 and the second server 16. In FIGS. 3 and 4, the processing is described from the viewpoint of the first computer 14 and from the viewpoint of the second server 16, respectively. With reference to FIG. 3, an illustrative embodiment of the imaging method 200, performed by the first computer 14, is diagrammatically shown as a flowchart. At 202, the first computer 14 is programmed to encrypt image data portions to generate encrypted image data portions. (This corresponds to operation 104 of FIG. 2). At 204, the first computer 14 is programmed to transmit the encrypted image data portions to the second server 16 (corresponding to operation 106). At 206, the first computer 14 is programmed to decrypt encrypted processed image data portions received from the second server 16 to produce processed image data portions and generating a processed image from the processed image data portions (corresponding to operation 110). At 208, the first computer is programmed to control the display device 24 to display the processed image or store the processed image in the PACS database 30 (corresponding to operation 112).

With reference to FIG. 4, an illustrative embodiment of the imaging method 300, performed by the second server 16, is diagrammatically shown as a flowchart. At 302, the second server 16 is programmed to receive encrypted image data portions from the first computer 14 via an electronic data network (not shown). At 304, the second server 16 is programmed to process the encrypted image data portions to produce processed encrypted image data portions. The processing does not include decrypting the encrypted image data portions. At 306, the second server 16 is programmed to transmitting the processed encrypted image data portions to the first computer 14 via the electronic data network.

In general, the ordering of the encrypted image data portions sent from the first computer 14 to the second server 16, on the one hand, and the ordering of the encrypted processed image data portions sent back from the second sever 16 to the first computer 14, on the other hand, should be the same. That is, the first computer 14 expects that: the first encrypted processed image data portion received back from the second server 16 is the processed version of the first encrypted image data portion sent by the first computer 14 to the second server 16; the second encrypted processed image data portion received back from the second server 16 is the processed version of the second encrypted image data portion sent by the first computer 14 to the second server 16; the third encrypted processed image data portion received back from the second server 16 is the processed version of the third encrypted image data portion sent by the first computer 14 to the second server 16; the fourth encrypted processed image data portion received back from the second server 16 is the processed version of the fourth encrypted image data portion sent by the first computer 14 to the second server 16; and so forth. This way, the first computer 14 knows which decryption algorithm and/or decryption algorithm parameters to use to decrypt each received encrypted processed image data portion, and knows where the resulting processed image data portion fits into the processed image (e.g., which voxel or voxel patch it corresponds to).

In a variant approach, the first computer 14 tags each encrypted image data portion with a unique identification code, and the second server 16 sends the encrypted processed image data portions back to the first computer 14 tagged with those same respective unique identification codes. At the first computer 14, the tags can then be used to determine where each encrypted processed image data portion fits into the processed image, and hence knows which decryption algorithm/parameters to use. In this variant approach, there is no requirement that the second server 16 send back the encrypted processed image data portions in the same order as it received them, which can simplify the data processing at the second server 16 (e.g., if some image data portions are processed faster than others using parallel processing then they can be sent back in different orders). However, this variant approach increases transmission bandwidth as the tags must be sent with the data portions.

EXAMPLE

The image data (typically including multi-dimensional data for each voxel) by the image acquisition device 12 is pre-processed by the client computer 14 in two randomization steps, then transferred to the cloud server 16 for processing. The results are then post-processed by the client computer 14 to recover the correctly analysed image. The individual data sets may consist of the multi-dimensional information of a single voxel, or of a small patch of voxels in spatial proximity.

In a first example embodiment, each voxel or patch is assigned an index i, with the corresponding multi-dimensional data set denoted $S_i$. In the encryption step (e.g. operation 104 of FIG. 2 or operation 202 of FIG. 3), each data set is transformed by an encryption algorithm represented by a transformation function T:

$$\tilde{S}_i = T(S_i, P_i) \qquad \text{Equation (1)}$$

where $P_i$ is the encryption algorithm parameters, e.g. preferably a set of randomly or pseudo-randomly chosen parameters for each voxel or patch i. The parameters $P_i$ used for each image data portion i are stored on the client computer 14. The transform T is chosen such that it does not affect the results of processing the data set except for a known reverse transformation T' (or, put another way, when the reverse transform T' is applied the result is to extracted the processed data as if the transform T had never been applied). With A representing the remote image analysis operation, this can be written as:

$$A(S_i) = T'(A(\tilde{S}_i), P_i) \qquad \text{Equation (2)}$$

where $A(\tilde{S}_i)$ is the encrypted processed image data portion received back from the second server 16 (e.g., the output by the operation 108 of FIG. 2 or by the operation 304 of FIG. 4) corresponding to the image data portion $S_i$, and $A(S_i)$ is the processed image data portion output by operation 110 of FIG. 2 or operation 206 of FIG. 3. In this way, the cloud server 16 has less information about the original data but can still perform the analysis. Only the client computer 14 is able to recover the correct results.

In one example, $S_i$ is assumed to represent the optical or magnetic resonance spectrum of a voxel in a pathologic sample. The remote processing operation of $A(S_i)$ returns the abundance of a specific substance in this voxel. Then the transformation could be a simple scaling by a random factor $P_i = f_i$:

$$T(S_i, f_i) = f_i S_i \qquad \text{Equation(3)}$$

The remote processing performed by the remote server 16 would still be able to check the spectrum for the substance in question and return the abundancy $\tilde{a} = A(f_i S_i) = f_i A(S_i)$, which would then also be scaled by the same factor. The client computer 14 could use the back transformation $$a = T'(\tilde{a}, f_i) = f_i^{-1} \tilde{a} \qquad \text{Equation (4)}$$

to recover the correct value for the substance abundance.

In another example, $S_i$ is assumed to represent the phase values of a patch of 5×5×5 voxels of a 3D MRI scan. The remote processing operation of $A(S_i)$ returns the tissue conductivity of the center voxel. The transformation T in this case could be a spatial mirroring or rotation of the voxels within the patch. The corresponding inverse mirror or rotation operation would obfuscate the original image but the absolute value of the tissue conductivity would be unchanged, so that the back transformation would by the identity transformation.

In another example embodiment, before transmitting the transformed data sets $\tilde{S}_i$ to the cloud server 16 from the client computer 14, the order of the data sets is randomized (i.e. mixed) by creating a random permutation. The permutation rule (translation table to undo the re-ordering afterwards) is stored locally on the client. The data sets are sent to the server in the permuted order. The cloud server 16 processes the data voxel-wise and returns the results in the same order. In the corresponding post-processing step, the client computer 14 uses the stored permutation rule to recover the correct ordering of the data sets.

In another embodiment, a pre-selection of voxels to be processed is performed on the client computer 14. For example, voxels containing very small signal amplitude (voxels outside the imaged body) could be excluded. In this way, the amount of data to be transferred is reduced and the number of transferred voxels does not correspond to the total number of voxels any more, so that the original image resolution is not known to the cloud server 16.

In another embodiment, each data set is assigned a unique random identifier. The data sets are again reordered in a random way. Both input and return pixel data would be labelled with their unique identifiers. In this way, the input and return order would not necessarily have to be the same, and the data processing could be performed asynchronously. This could be interesting for setups where several imaging systems of a local network send data to a remote processing unit, introducing even more randomization by mixing the pixels of different sources, or for parallelization of the processing by the cloud server 16.

In another embodiment, the data sets of several images are mixed by a random permutation. Using the stored permutation rules, it is possible to re-assign the returned analysed data to the different images and to the correct pixel position within the images.

In another embodiment, two or more servers or computers 14 and 16 are available for image processing, offering the same capabilities. By distributing data sets to a random selection of servers, each server has less information available, which increases data security.

In another embodiment, the client computer 14 produces additional synthetic data sets and places them at random positions among the set of transferred real data packages. In this way, an additional level of security by obfuscation is added, making it harder for the server to reconstruct image information. The synthetic data sets can include modified versions of real voxel data (for example, noise added), linear combinations of data from several real data sets, or completely synthetic or arbitrary data. The processed results of these data sets will be ignored by the client.

In another embodiment, an additional proxy or relay server (not shown) collects the data sets from the client computer 14 and pass them on to the cloud server 16 anonymously. In this way, the cloud server 16 are not able to group data sets according to their origin, which again makes it more difficult to obtain any useful information about the original images. End-to-end encryption of the data packages further makes it impossible for the proxy or relay server to collect information about the image content.

In another embodiment, each pixel data set is combined with an identifier specifying the type of analysis algorithm to use. This would allow the server to provide several different analysis algorithms and apply them to the data sets from different measurements in the correct way.

Figure 5:
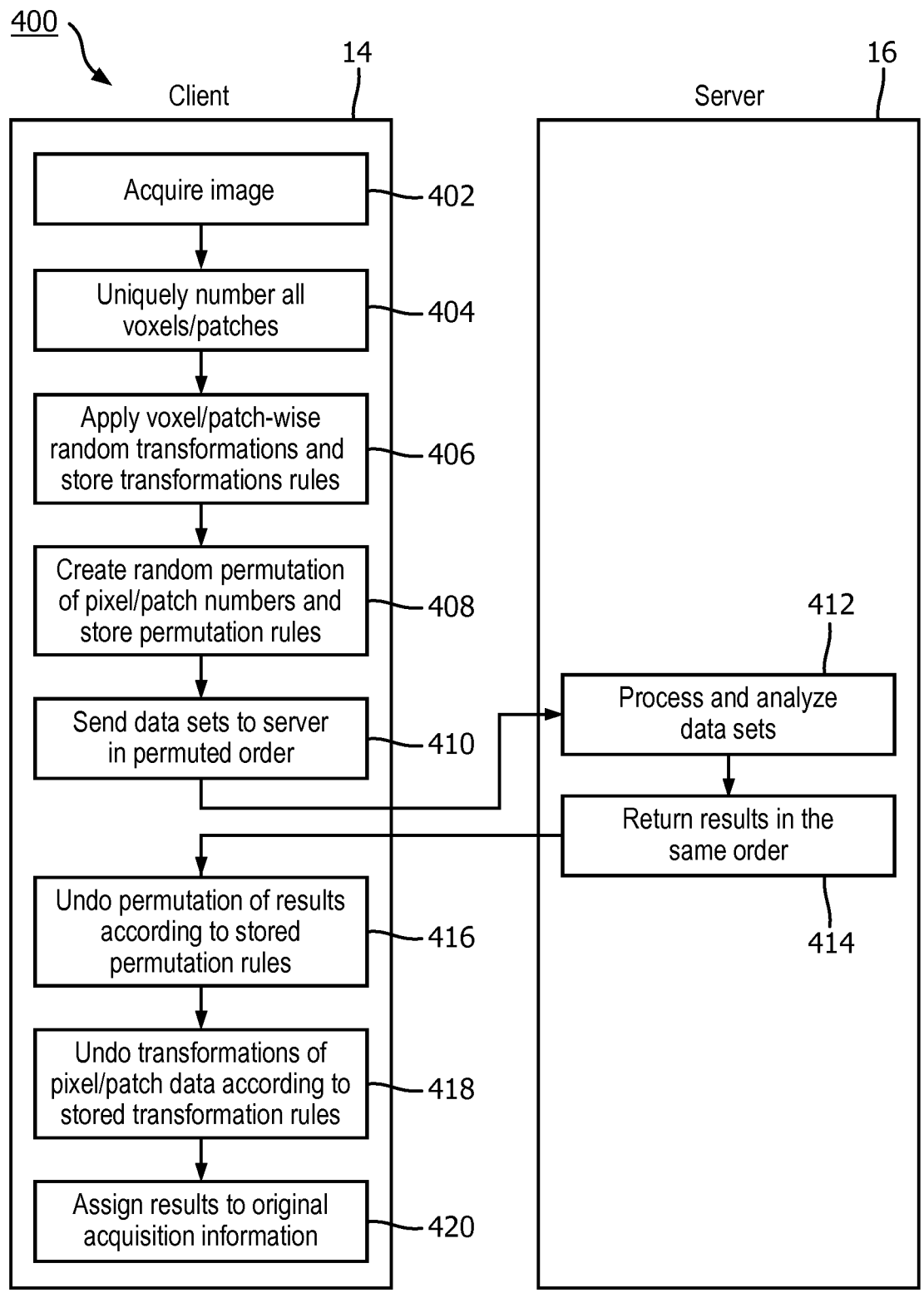

FIG. 5 shows another example flowchart of the imaging method 400. At 402, images are acquired. At 404, all voxels or patches of the images are uniquely numbered. At 406, random transformations are applied on a voxel or patch basis and the transformation rules are stored. At 408, a random permutation of the voxel/patch numbers are created and the permutation data is stored. At 410, the data sets are sent from the client computer 14 to the cloud server 16. At 412, the data sets are processed and analyzed. At 414, the results are returned in the same order. At 416, the permutation of the results are undone according to the stored permutation rules. At 418, the transformations of the voxel/patch data are undone according to the stored transformation rules. At 420, the results are assigned to the original acquisition data of the acquired images.

The disclosure has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A non-transitory storage medium storing instructions readable and executable by a first computer to perform an image processing method comprising:
   encrypting image data portions to generate encrypted image data portions;
   transmitting the encrypted image data portions from the first computer to a second server different from the first computer;
   decrypting encrypted processed image data portions received at the first computer from the second server to produce processed image data portions and generating a processed image from the processed image data portions; and
   controlling a display device to display the processed image or storing the processed image in a database;
   wherein the encrypting of each image data portion indexed by i comprises performing the transform:

$$\tilde{S}_i = T(S_i, P_i)$$

where $S_i$ represents multi-dimensional data of the image data portion indexed by i, T represents the transform, $P_i$ represents parameters of the transform T for the image data portion indexed by i, and $\tilde{S}$ represents the encrypted image data portion.

2. The non-transitory storage medium of claim 1, wherein:
   each image data portion comprises an individual voxel magnetic resonance (MR) spectrum; and
   the encrypting comprises scaling each individual voxel MR spectrum by a voxel-specific scaling factor.

3. The non-transitory storage medium of claim 1, wherein the encrypting employs different encryption algorithms or encryption algorithm parameters for encrypting different image data portions.

4. An image processing method, comprising:
   at a first computer, encrypting image data portions to generate encrypted image data portions, wherein each image data portion comprises a patch of voxels and the encrypting comprises applying at least one of a spatial mirroring operation and a spatial rotation operation to the patch of voxels;
   at a second server, processing the encrypted image data portions to produce processed encrypted image data portions;
   at the first computer, decrypting the encrypted processed image data portions to produce processed image data portions and generating a processed image from the processed image data portions; and
   controlling a display device to display the processed image or storing the processed image in a database.

5. The image processing method of claim 4, wherein:
   each image data portion comprises an individual voxel magnetic resonance (MR) spectrum; and
   the processing of the encrypted image data portions includes applying a spectral imaging analysis or a magnetic resonance fingerprint analysis on a per-voxel basis to each individual voxel MR spectrum.

6. The image processing method of claim 5, wherein the encrypting comprises scaling each individual voxel MR spectrum by a voxel-specific scaling factor.

7. The image processing method of claim 4, wherein
   the processing of the encrypted image data portion includes applying a conductivity analysis or kernel filter analysis to each encrypted patch of voxels.

8. The image processing method of claim 4, wherein the encrypting of each image data portion indexed by i comprises performing the transform:

$$\tilde{S}_i = T(S_i, P_i)$$

where $S_i$ represents multi-dimensional data of the image data portion indexed by i, T represents the transform, $P_i$ represents parameters of the transform T for the image data portion indexed by i, and $\tilde{S}$ represents the encrypted image data portion.

9. The image processing method of claim 4, wherein the encrypting employs different encryption algorithms or encryption algorithm parameters for encrypting different image data portions.

10. The image processing method of claim 4, further comprising:
    at the first computer, generating a data stream comprising the encrypted image data portions; and
    transmitting the data stream from the first computer to the second server.

11. The image processing method of claim 10, wherein the generating of the data stream comprises:
    mixing an ordering of the image data portions in the data stream.

12. The image processing method of claim 10, wherein the generating of the data stream comprises:
    adding extra encrypted image data portions to the data stream wherein the processed image data portions corresponding to the extra encrypted image data portions are not used in generating the processed image.

13. The image processing method of claim 10, wherein the image data portions are extracted from two or more images, the generating of the data stream comprises mixing the image data portions of the two or more images in the data stream, and the generating of the processed image comprises generating a processed image corresponding to each image of the two or more images from the processed image data portions of that image.

14. The image processing method of claim 4, wherein the processing, at the second computer, of the encrypted image data portions to produce the processed encrypted image data portions does not include decrypting the encrypted image data portions at the second server.

* * * * *